United States Patent [19]

Hoehn

[11] 4,248,881

[45] Feb. 3, 1981

[54] IMIDAZOLYLETHOXYMETHYL DERIVATIVES OF PYRAZOLE

[75] Inventor: Hans Hoehn, Tegernheim, Fed. Rep. of Germany

[73] Assignee: E. R. Squibb & Sons, Inc., Princeton, N.J.

[21] Appl. No.: 105,688

[22] Filed: Dec. 20, 1979

[51] Int. Cl.³ .................... A01N 43/50; C07D 403/00
[52] U.S. Cl. ................... 424/273 P; 548/336
[58] Field of Search .................. 548/336; 424/273 P

[56] References Cited

U.S. PATENT DOCUMENTS

| | | | |
|---|---|---|---|
| 3,658,813 | 4/1972 | Godefroi et al. | 548/342 |
| 3,717,655 | 2/1973 | Godefroi et al. | 548/342 |
| 3,991,201 | 11/1976 | Heeres et al. | 424/273 |
| 4,059,705 | 11/1977 | Walker | 424/273 R |
| 4,062,966 | 12/1977 | Gymer | 424/273 R |
| 4,107,314 | 8/1978 | Cox et al. | 424/263 |
| 4,159,380 | 6/1979 | Hoehn | 548/341 |

OTHER PUBLICATIONS

Chem. Abstracts 76: 72516q.
Godefroi et al., J. Med. Chem. 12, pp. 784–791 (1969).
Heeres et al., J. Med. Chem. 19(9), pp. 1148–1155 (1976).
Heeres et al., J. Med. Chem. 20(11), pp. 1511–1520 (1977).
Walker, J. Med. Chem. 21(12), pp. 1335–1338 (1978).

*Primary Examiner*—Ethel G. Love
*Attorney, Agent, or Firm*—Lawrence S. Levinson; Burton Rodney

[57] ABSTRACT

Compounds are provided having the structure

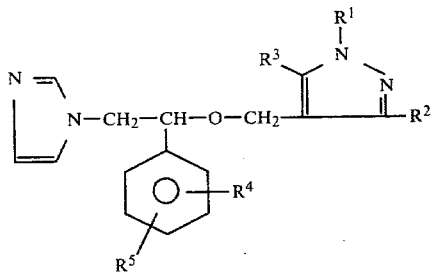

wherein $R^1$ and $R^2$ may be the same or different and each may be hydrogen, lower alkyl, phenyl-lower alkyl, phenyl, substituted phenyl wherein the phenyl group bears one halogen, hydroxy, lower alkyl, lower alkylthio, cyano or nitro group; $R^3$ is halogen; and $R^4$ and $R^5$ may be the same or different and each may be hydrogen, hydroxy, lower alkoxy, lower alkylthio or halogen.

These compounds as well as acid addition salts thereof are useful as antimicrobial agents.

11 Claims, No Drawings

IMIDAZOLYLETHOXYMETHYL DERIVATIVES OF PYRAZOLE

SUMMARY OF THE INVENTION

This invention relates to new imidazolyl-ethoxymethyl derivatives of pyrazole and the acid addition salts of these compounds. These new compounds have the formula

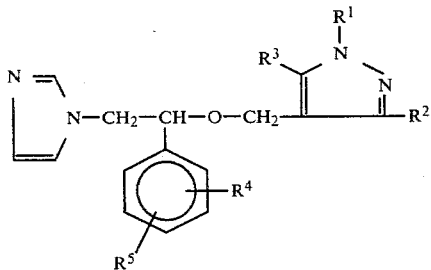

The symbols have the following meaning in formula I and throughout the specification:

$R^1$ and $R^2$ may be the same or different and each may be hydrogen, lower alkyl, phenyl-lower alkyl, phenyl, or substituted phenyl wherein the phenyl group bears one halogen, hydroxy, lower alkyl, lower alkylthio, cyano or nitro group; $R^3$ is halogen; and $R^4$ and $R^5$ may be the same or different and each may be hydrogen, hydroxy, lower alkoxy, lower alkylthio or halogen.

The new compounds of formula I are useful as antimicrobial agents, especially against fungi strains.

DETAILED DESCRIPTION OF THE INVENTION

The lower alkyl groups include straight or branched chain hydrocarbon groups containing 1 to 7 carbon atoms. Examples include methyl, ethyl, propyl, isopropyl, etc. The lower alkoxy and lower alkylthio groups include such lower alkyl groups bonded to an oxygen or sulfur, respectively, e.g., methoxy, ethoxy, propoxy, butoxy, t-butoxy, methylthio, ethylthio, propylthio, butylthio, isobutylthio, etc. In all of these the $C_1$–$C_4$, especially $C_1$–$C_2$, lower alkyl groups are preferred.

The halogens are the four common halogens, chlorine and bromine being preferred in that order. Preferably, but not necessarily, all halogens in a single compound are the same.

Preferred embodiments of this invention are compounds of formula I wherein $R^1$ is phenyl or substituted phenyl, such as halophenyl, $R^2$ is lower alkyl, such as methyl or ethyl, and $R^3$, $R^4$ and $R^5$ are halogen, such as chloro, and the hydrohalide salts such as hydrochloride salts thereof.

The new compounds of formula I are formed by the following series of reactions.

Vilsmeier-formylation of pyrazolones of the formula

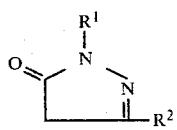

give rise to 4-carboxaldehydes of the formula

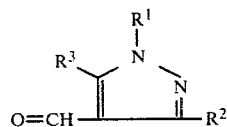

wherein $R^3$ represents a halogen atom, preferably chlorine. Reduction of the carboxaldehydes (III) by means of a reducing agent, e.g., lithium aluminum hydride or sodium borohydride and the like, gives the alcohol of the formula

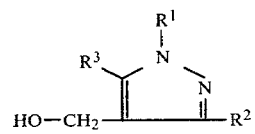

which in turn is converted to the halomethyl derivative of the formula

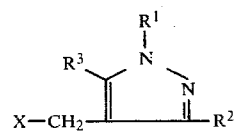

wherein X is Cl or Br, by treating the alcohol of formula IV with an inorganic acid halide, such as thionyl chloride, phosphorous oxybromide, etc.

The product of formula I is then prepared by reaction of the halomethyl compound of the formula V with a substituted 1-(phenyl)-2-(1H-imidazol-1-yl)-ethanol of the formula

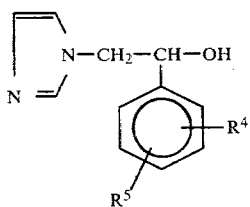

The inorganic acid formed during the reaction is neutralized by a base, e.g., alkali metal hydroxide, carbonate, amine, alcoholate or other similar bases known in the art.

The compounds of formula III, which are used as starting materials, are disclosed in the literature, for example, in "The Chemistry of Heterocyclic Compounds", Vol. 20, Pyrazolones, Pyrazolidones and Derivatives, edited by Richard H. Wiley and Paul Wiley (published by John Wiley and Sons, New York, London, Sydney 1964). The compounds of formula VI, which are also used as starting materials, are produced by the general methods described in J. of Med. Chemistry, Vol. 12, 784 (1969).

The compounds of formula I form salts which are also part of this invention. The salts include acid addition salts, particularly the non-toxic, physiologically acceptable members. The bases of formula I form salts by reactions with one or more equivalents of any of a variety of the common inorganic and organic acids providing acid addition salts including for example, hydrohalides (especially hydrochloride and hydrobromide), sulfate, nitrate, borate, phosphate, oxalate, tartrate, maleate, citrate, acetate, ascorbate, succinate, benzenesulfonate, methanesulfonate, cyclohexanesulfamate and toluenesulfonate. The acid addition salts frequently provide a convenient means for isolating or purifying the product, e.g., by forming and precipitating a salt (which is not necessarily non-toxic) in an appropriate medium in which the salt is insoluble, then after separation of the salt, neutralizing with a base, such as barium hydroxide or sodium hydroxide, to obtain the free base of formula I. Other salts may then be formed from the free base by reaction with one or more equivalents of acid containing the desired acid group.

The new compounds of formula I and their salts are useful as anti-fungal and anti-bacterial agents and may be used to combat infections in various mammalian species, such as mice, rats, dogs, guinea pigs and the like, particularly those due to organisms such as *Candida albicans*, as well as organisms such as *Trichomonas vaginalis* or *Trichophyton mentagrophytes*. For example, a compound or mixture of compounds of formula I or physiologically acceptable acid addition salt thereof can be administered orally to an infected animal, e.g., to a mouse, in an amount of about 5 to 25 mg per kg per day in 2 to 4 divided doses. These may be conventionally formulated in a tablet, capsule or elixir containing about 10 to 250 mg per dosage unit, by compounding the active substance or substances with the conventional excipient, vehicle, binder, preservative, flavor, etc., as called for by accepted pharmaceutical practice. Preferably they are applied topically, e.g., intravaginally in a lotion or in a conventional cream base at a concentration of about 0.01 to 3 percent by weight for a period of about 3 to 7 days, two to four times daily.

The following Examples represent preferred embodiments of the present invention. All temperatures are in degrees Centigrade (°C.).

EXAMPLE 1

5-Chloro-4-[[1-(2,4-dichlorophenyl)-2-(1H-imidazol-1-yl)ethoxy]methyl]-3-methyl-1-phenyl-1H-pyrazole, hydrochloride (1:1)

A.

5-Chloro-3-methyl-1-phenylpyrazol-4-yl-carboxaldehyde

A mixture of 16.2 g of N-methylformanilide (0.12 mol) and 30.7 g (18.3 ml) of phosphorous oxychloride (0.2 mol) is allowed to stand for 40 minutes. Then 17.4 g of 3-methyl-1-phenyl-pyrazol-5-one (0.1 mol) are added to the stirred mixture which is heated in an oil bath to 110° C. While cooling the flask with tap water, 160 ml of water and 130 ml of half-concentrated aqueous ammonia are added to the mixture, causing formation of a sticky product, which after decanting of the aqueous solution and trituration with ether becomes crystalline. The 5-chloro-3-methyl-1-phenylpyrazol-4-yl-carboxaldehyde (16 g) is filtered off and recrystallized from ligroin, m.p. 133°–134° C.

B.

5-Chloro-4-hydroxymethyl-3-methyl-1-phenylpyrazole

To 9.7 g of 5-chloro-3-methyl-1-phenyl-pyrazol-4-yl-carboxaldehyde (0.044 mol) suspended in 150 ml of methanol and cooled to 10° C. is added portionwise 2.5 g of sodium borohydride while stirring. The reaction temperature is kept between 10° and 15° C. Stirring is continued for an additional five hours and the mixture is allowed to stand overnight. While cooling with ice, 25 ml of water are added dropwise and the solution is adjusted to pH 5-6 by addition of concentrated hydrochloric acid. Then methanol is distilled off and the residue is extracted twice with chloroform. The combined chloroform extracts are dried and then evaporated. The oily 5-chloro-4-hydroxymethyl-3-methyl-1-phenylpyrazole, which soon begins to crystallize, is recrystallized from hexane, and yields 6.17 g (63%), m.p. 79°–83° C.

C.

5-Chloro-4-chloromethyl-3-methyl-1-phenylpyrazole 6.1 g of 5-chloro-4-hydroxymethyl-3-methyl-1-phenylpyrazole are added portionwise to 50 ml of thionylchloride. The mixture is refluxed for 2 hours, the excess thionylchloride distilled off, the oily product treated with water and then extracted with ether. The dried ethereal extract is evaporated in vacuo yielding 6.1 g of oily 5-chloro-4-chloromethyl-3-methyl-1-phenylpyrazole which, without further purification, is used in the next reaction step.

D.

5-Chloro-4-[[1-(2,4-dichlorophenyl)-2-(1H-imidazol-1-yl)ethoxy]methyl]-3-methyl-1-phenyl-1H-pyrazole, hydrochloride (1:1)

In a three-necked flask, fitted with stirrer, reflux condenser and gas inlet tube are introduced 24.3 g of sodium hydroxide (0.61 mol) and 23 ml of water. While passing nitrogen through the flask, the solution is cooled to 45° C. and then are added 6.5 g of 1-(2,4-dichlorophenyl)-2-(1H-imidazol-1-yl)ethanol (0.025 mol), 0.25 g of benzyltrimethyl-ammonium chloride and 40 ml of tetrahydrofuran. To the mixture, which is warmed to 50° C., are added 6.1 g of 5-chloro-4-chloromethyl-3-methyl-1-phenylpyrazole (0.025 mol). The mixture is stirred vigorously for 3 hours at 60° C. using a water bath. Then the warm mixture is transferred into a separating funnel, and the lower aqueous sodium hydroxide is extracted with 15 ml of tetrahydrofuran. The combined tetrahydrofuran layers are dried with sodium sulfate, trated with charcoal and distilled off to half of their volume. Addition of ether to the mixture causes a deposit of an oily side product. The clear solution (containing 5-chloro-4-[[1-(2,4-dichlorophenyl)-2-(1H-imidazol-1-yl)ethoxy]methyl]-3-methyl-1-phenyl-1H-pyrazole) is decanted and after addition of ethereal hydrochloric acid, 9 g of 5-chloro-4-[[1-(2,4-dichlorophenyl)-2-(1H-imidazol-1-yl)-ethoxy]methyl]-3-methyl-1-phenyl-1H-pyrazole, hydrochloride (1:1) precipitate. Recrystallization from acetonitrile gives 6.9 g=55%, m.p. 184°–185° C.

EXAMPLE 2

5-Chloro-4-[[1-(2,4-dichlorophenyl)-2-(1H-imidazol-1-yl)ethoxy]methyl]-3-methyl-1-(m-chlorophenyl)-1H-pyrazole, hydrochloride (1:1)

Following the procedure of Example 1, except substituting 5-chloro-3-methyl-1-(m-chlorophenyl)pyrazol-4-yl-carboxaldehyde for 5-chloro-3-methyl-1-phenyl-pyrazol-4-yl-carboxaldehyde, the title compound is obtained, m.p. 180°.

EXAMPLE 3

5-Chloro-4-[[1-(2,4-dichlorophenyl)-2-(1H-imidazol-1-yl)ethoxy]methyl]-3-methyl-1-(p-chlorophenyl)-1H-pyrazole, hydrochloride (1:1)

Following the procedure of Example 1, except substituting 5-chloro-3-methyl-1-(p-chlorophenyl)pyrazol-4-yl-carboxaldehyde for the 5-chloro-3-methyl-1-phenylpyrazol-4-yl-carboxaldehyde, the title compound is obtained, m.p. 203°.

The following additional products of formula C are obtained by the procedure of Example 1 by employing as starting materials 4-carboxaldehydes of formula A and substituted 1-(phenyl)-2-(1H-imidazol-1-yl)ethanols of formula B.

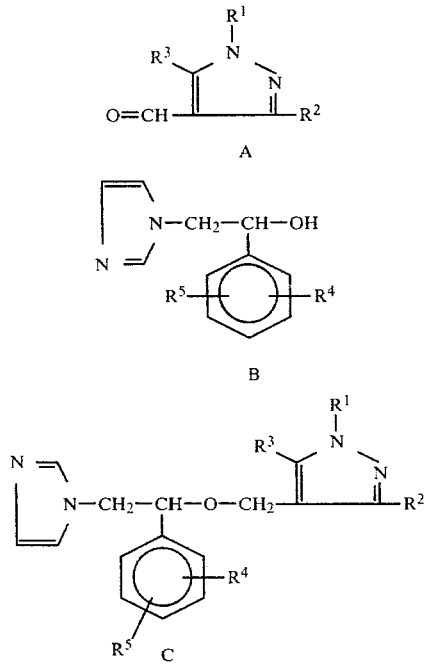

| Ex. No. | $R^1$ | $R^2$ | $R^3$ | $R^4$ | $R^5$ |
|---|---|---|---|---|---|
| 4. | H | H | Cl | H | H |
| 5. | H | $C_2H_5$ | Br | o-OH | p-OH |
| 6. | $CH_3$ | H | Cl | o-$CH_3$ | H |
| 7. | $C_6H_5CH_2$ | $C_6H_5CH_2$ | Cl | H | H |
| 8. | $C_2H_5$ | $CH_3$ | Cl | p-$CH_3S$ | H |
| 9. | p-OH$C_6H_4$ | $CH_3$ | Br | o-$CH_3$ | p-Cl |
| 10. | $CH_3$ | $CH_3$ | Cl | p-$CH_3O$ | H |
| 11. | o-$CH_3C_6H_4$ | H | Cl | o-Br | p-Br |
| 12. | $C_6H_5$ | $C_6H_5$ | Br | H | H |
| 13. | H | $C_6H_5$ | Cl | o-Cl | p-Cl |
| 14. | p-$CH_3SC_6H_4$ | H | Cl | H | m-Cl |
| 15. | m-$NO_2C_6H_4$ | $C_2H_5$ | Cl | H | o-$CH_3O$ |
| 16. | H | p-$CNC_6H_4$ | Cl | o-Cl | p-Cl |
| 17. | $C_6H_5$ | $C_3H_7$ | Cl | p-$CH_3S$ | H |
| 18. | $C_3H_7$ | $C_2H_5$ | Cl | o-OH | H |
| 19. | $C_6H_5$ | H | Br | H | H |
| 20. | H | o-$C_6H_5CH_2$ | Cl | H | H |

EXAMPLE 21

5-Chloro-4-[[1-(2,4-dichlorophenyl)-2-(1H-imidazol-1-yl)ethoxy]methyl]-3-methyl-1-(phenylmethyl)-1H-pyrazole, hydrochloride (1:1)

Following the procedure of Example 1, except substituting 5-chloro-3-methyl-1-(phenylmethyl)-pyrazol-4-yl-carboxaldehyde for the 5-chloro-3-methyl-1-phenylpyrazol-4-yl-carboxaldehyde, the title compound is obtained, m.p. 151°–152° C.

What is claimed is:

1. A compound of the formula

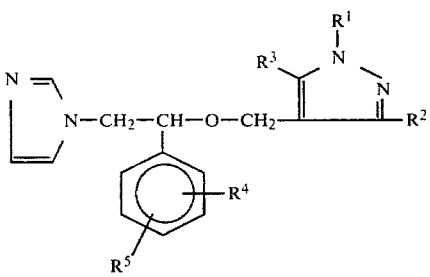

wherein $R^1$ and $R^2$ may be the same or different and each is hydrogen, lower alkyl, phenyl-lower alkyl, phenyl, or substituted phenyl wherein the phenyl group bears one halogen, hydroxy, lower alkoxy, lower alkyl, lower alkylthio, cyano or nitro group, $R^3$ is halogen, and $R^4$ and $R^5$ may be the same or different and each is hydrogen, hydroxy, lower alkoxy, lower alkylthio or halogen, and non-toxic physiologically acceptable acid addition salts thereof.

2. The compound as defined in claim 1 wherein $R^1$ is phenyl or substituted phenyl.

3. The compound as defined in claim 1 wherein $R^2$ is lower alkyl.

4. The compound as defined in claim 1 wherein $R^3$ is chloro.

5. The compound as defined in claim 1 wherein $R^4$ and $R^5$ are each halogen.

6. The compound as defined in claim 1 in the form of its hydrochloride salt.

7. The compound as defined in claim 1 having the name 5-chloro-4-[[1-(2,4-dichlorophenyl)-2-(1H-imidazol-1-yl)ethoxy]methyl]-3-methyl-1-phenyl-1H-pyrazole or its hydrochloride salt.

8. The compound as defined in claim 1 having the name 5-chloro-4-[[1-(2,4-dichlorophenyl)-2-(1H-imidazol-1-yl)ethoxy]methyl]-3-methyl-1-(m-chlorophenyl)-1H-pyrazole or its hydrochloride salt.

9. The compound as defined in claim 1 having the name 5-chloro-4-[[1-(2,4-dichlorophenyl)-2-(1H-imidazol-1-yl)ethoxy]methyl]-3-methyl-1-(p-chlorophenyl)-1H-pyrazole or its hydrochloride salt.

10. An antimicrobial composition comprising an antimicrobially effective amount of a compound as defined in claim 1 and a pharmaceutically acceptable carrier therefor.

11. A method for treating bacterial or fungal infections in mammals which comprises administering to a mammalian host an anti-bacterial or antifungal effective amount of a compound as defined in claim 1.

* * * * *